(12) United States Patent
Ohta et al.

(10) Patent No.: US 7,191,010 B2
(45) Date of Patent: Mar. 13, 2007

(54) BUILT-IN-EYE EYESIGHT STIMULATING APPARATUS

(75) Inventors: Jun Ohta, Nara (JP); Shigeru Nishimura, Chiba (JP); Kohtaro Idegami, Ishikawa (JP); Norikatsu Yoshida, Nara (JP); Keiichiro Kagawa, Nara (JP)

(73) Assignee: Nidek Co., Ltd., Aichi (JP)

( * ) Notice: Subject to any disclaimer, the term of this patent is extended or adjusted under 35 U.S.C. 154(b) by 615 days.

(21) Appl. No.: 10/469,342

(22) PCT Filed: Feb. 28, 2002

(86) PCT No.: PCT/JP02/01874

§ 371 (c)(1),
(2), (4) Date: Aug. 28, 2003

(87) PCT Pub. No.: WO02/067829

PCT Pub. Date: Sep. 6, 2002

(65) Prior Publication Data

US 2004/0098067 A1 May 20, 2004

(30) Foreign Application Priority Data

Feb. 28, 2001 (JP) ............... P2001-055772
Sep. 4, 2001 (JP) ............... P2001-268074

(51) Int. Cl.
*A61N 1/00* (2006.01)
(52) U.S. Cl. ...................................... 607/54
(58) Field of Classification Search ............ 607/53, 607/54, 2
See application file for complete search history.

(56) References Cited

U.S. PATENT DOCUMENTS

| 5,109,844 | A  | * | 5/1992  | de Juan et al. ......... 607/53 |
| 6,393,327 | B1 | * | 5/2002  | Scribner ............... 607/54 |
| 6,804,560 | B2 | * | 10/2004 | Nisch et al. ........... 607/54 |
| 2002/0091422 | A1 | * | 7/2002 | Greenberg et al. ...... 607/54 |

FOREIGN PATENT DOCUMENTS

| JP | 2001-204757 A   | 7/2001  |
| WO | WO 90/00912 A1  | 2/1990  |
| WO | WO 94/26209 A1  | 11/1994 |
| WO | WO 96/39221 A1  | 12/1996 |
| WO | WO 97/05922 A2  | 2/1997  |
| WO | WO 99/45870 A1  | 9/1999  |

* cited by examiner

*Primary Examiner*—Mark Bockelman
(74) *Attorney, Agent, or Firm*—Sughrue Mion, PLLC

(57) ABSTRACT

An object of the invention is to provide an intraocular implant-type vision stimulating unit which is capable of outputting a bipolar pulse signal in a simple constitution, and is highly sensitive, compact, and low power consumptive.

In the invention, an intraocular implant-type vision stimulating unit for artificially generating the vision or a portion of the vision includes: a photoelectric conversion circuit for converting incoming light into an electrical signal; a pulse conversion circuit for converting the electrical signal outputted from the photoelectric conversion circuit into an electric pulse signal of a frequency corresponding to a magnitude thereof, and for outputting the same; a waveform shaping circuit for converting the pulse signal outputted from the pulse conversion circuit into a bipolar pulse signal, and for outputting the same; a power supply circuit for supplying electric power to each of the circuits, wherein the bipolar pulse signal is imparted to a retinal region through an electrode.

16 Claims, 16 Drawing Sheets

FIG. 2 (a)
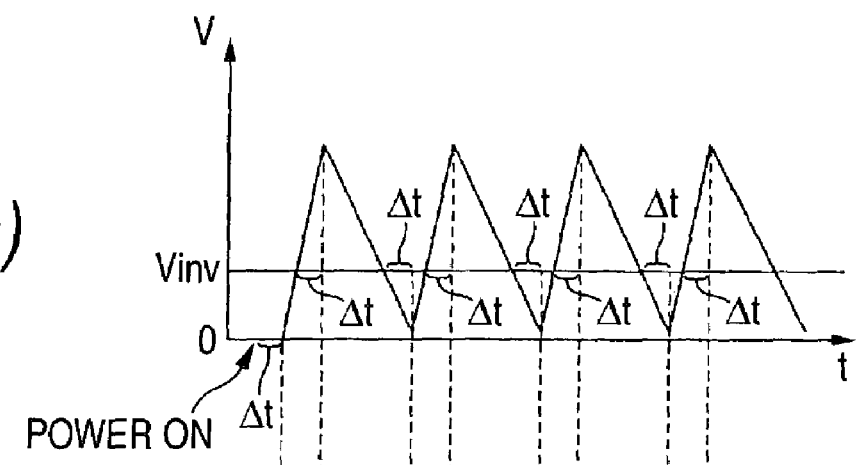
FIG. 2 (b)
FIG. 2 (c)
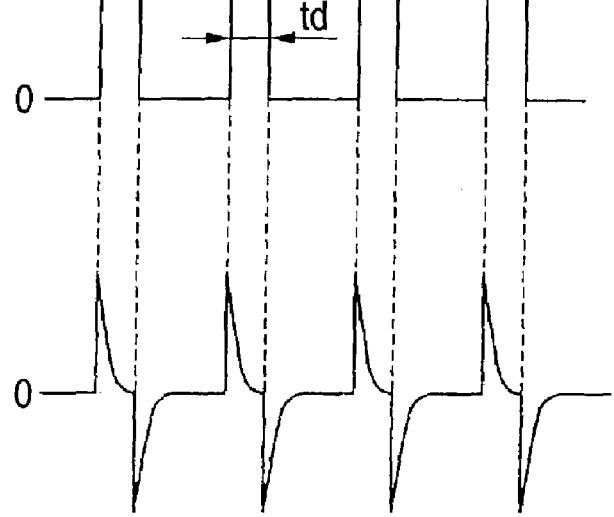

PERIOD T

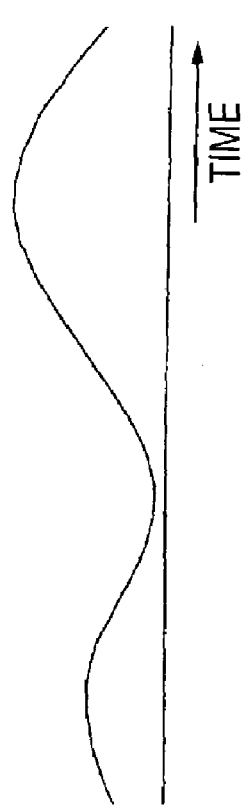
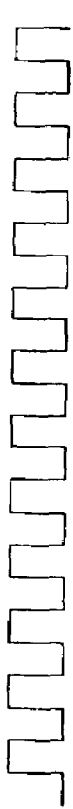
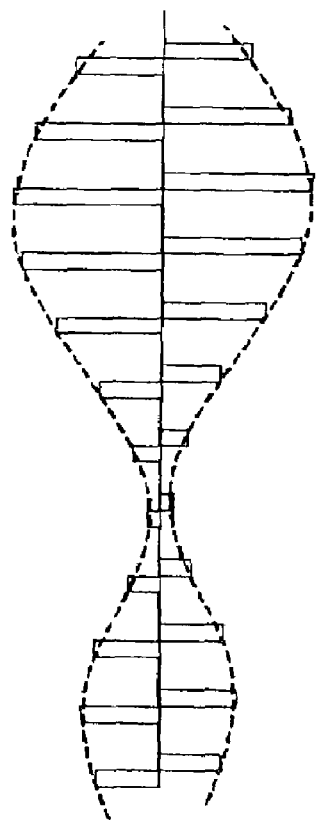
FIG. 13 (a) PHOTOELECTRIC CONVERSION WAVEFORM
FIG. 13 (b) SAMPLING PULSES
FIG. 13 (c) UNIPOLAR PULSE AMPLITUDE MODULATION WAVEFORM
FIG. 13 (d) BIPOLAR PULSE AMPLITUDE MODULATION WAVEFORM

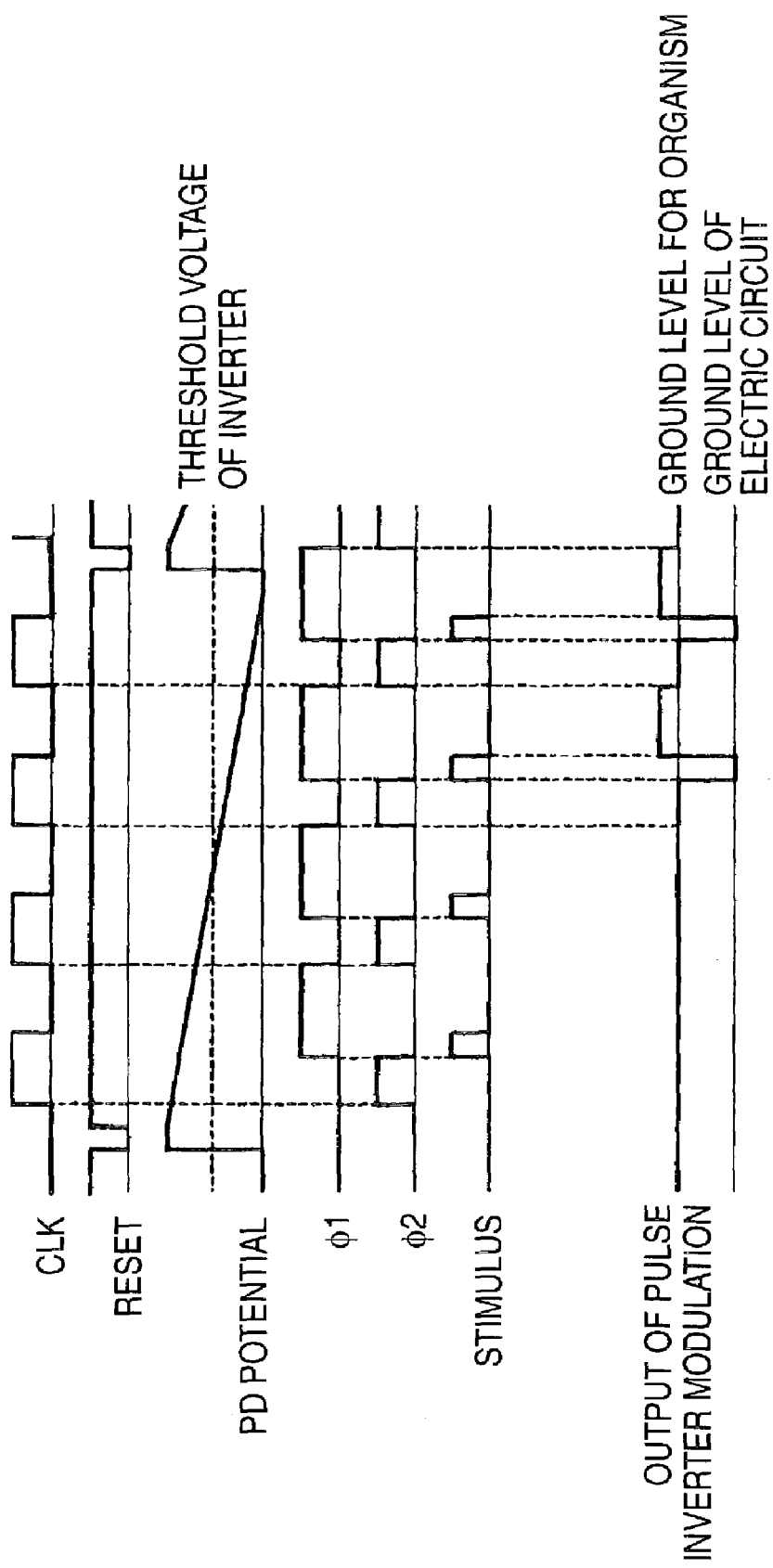

BUILT-IN-EYE EYESIGHT STIMULATING APPARATUS

TECHNICAL FIELD

The present invention relates to an intraocular implant-type vision stimulating unit for artificially generating the vision or a portion of the vision.

BACKGROUND ART

A conventional intraocular implant-type vision stimulating unit is so arranged that incoming light from outside the eye is photoelectrically converted by light receiving elements disposed in the form of a two-dimensional array, implanted beneath the retina, and adapted to effect only photoelectric conversion, and a retinal region is stimulated by electrical signals so as to obtain vision artificially.

FIG. 5 is a diagram illustrating equivalent circuits of micro photodiodes disclosed in JP-T-11-506662. In FIG. 5, filters are respectively inserted in pin photodiodes 101 and 104 so that their p sides respond to the visible light and their n sides respond to the near infrared light. The pin photodiode 101 whose n side becomes a light receiving surface with respect to incoming light 107 and the pin photodiode 104 whose p side becomes a light receiving surface with respect to the incoming light 107 are formed as a pair.

In the conventional vision stimulating unit constructed as described above, the incoming light 107 is first subjected to photoelectric conversion by the photodiodes 101 and 104, and as electron and hole pairs are generated to form a photoelectric current. Since the photoelectric current flows out from the p side, a positive/negative bipolar current, in which a negative current is obtained from an n-side electrode 103 of the pin photodiode 101 and a positive current is obtained from a p-side electrode 106 of the pin photodiode 104, is obtained by this pair of photodiodes. Accordingly, as the pair of electrodes 103 and 106 are disposed in a retinal region, it is possible to impart a positive/negative bipolar electrical stimulus. In practice, in this conventional example, the near infrared light generated outside is caused to strike the retinal surface at an appropriate timing, and is combined with the visible light 107 inputted as image information from the outer world, thereby generating a positive/negative bipolar current so as to prevent the deterioration of the body issue. For this reason, a filter for near infrared light is fitted in the pin photodiode 101. Further, as the pairs of photodiodes thus structured are disposed in the two-dimensional form, image information from the outer world is used as a stimulus pattern on the retinal surface.

In the conventional example shown in FIG. 5, characteristics of the intraocular implant-type photodiodes under ordinary room light (illuminance Eo=1,000 luxes or thereabouts) are considered by assuming that the intensity (quantity) of light of the incoming light is P, and that a photoelectric current flowing between a p-side electrode 102 and the n-side electrode 103 of the pin photodiode 101 is Iph. In a case where the eyeball is considered as a lens, if the focal length is F=6 mm and the effective aperture is D=8 mm, the f-number becomes F=f/D=2.0. At this time, if it is assumed that reflectivity of the object is R=1.0 and that the transmittance of the eyeball is T=1.0, the illuminance E at the retinal surface becomes E=60 luxes from the following:

$$E = \frac{RT}{4F^2} E_0$$

Accordingly, in a case where the light receiving surface of the photodiode is set to 20×20 μm² in the case of the aforementioned publication, the quantity P of incoming light upon the photodiode becomes P=30 pW or thereabouts since 1 lux is 0.14 μW/m² with respect to the light with a wavelength of 550 nm. If the light-receiving sensitivity of the photodiode is assumed to be S=0.1 A/W, the photoelectric current is Iph=PS=3 pA or thereabouts. It can thus be understood that an extremely small current is generated. Since the amount of charge necessary for stimulation is the to be 100 nC/m² or more, the necessary stimulation time becomes 0.1 sec., and is therefore not realistic. In addition, the conventional example, which requires two photodiodes to output a positive/negative bipolar current, is disadvantageous to the implant-type vision stimulating unit for which the smallest possible size is required.

In addition, with this conventional example, the pulse signal cannot be generated by the circuit implanted in the eye, and there is a drawback in that a device is required for causing the infrared light generated outside to enter the eye for the purposes of generation and modulation of the pulse signal.

In view of the above-described problems of the conventional art, an object is to provide an intraocular implant-type vision stimulating unit which is highly sensitive, compact, and low power consumptive.

Another object is to provide an intraocular implant-type vision stimulating unit which is capable of outputting a bipolar pulse signal in a simple constitution.

DISCLOSURE OF THE INVENTION

To overcome the above-described problems, the invention is characterized by having the following constitutions:

(1) An intraocular implant-type vision stimulating unit for artificially generating the vision or a portion of the vision, comprising:
a photoelectric conversion circuit which converts incoming light into an electrical signal;
a pulse conversion circuit which converts the electrical signal outputted from the photoelectric conversion circuit into an electric pulse signal of a frequency corresponding to a magnitude of the electrical signal, and outputs the electric pulse signal;
a waveform shaping circuit which converts the pulse signal outputted from the pulse conversion circuit into a bipolar pulse signal, and outputs the bipolar pulse signal;
a power supply circuit which supplies electric power to each of the circuits,
wherein the bipolar pulse signal is imparted to a retinal region through an electrode.

(2) The intraocular implant-type vision stimulating unit according to (1), wherein the photoelectric conversion circuit, the pulse conversion circuit, and the waveform shaping circuit are implanted beneath the retina.

(3) The intraocular implant-type vision stimulating unit according to (1), wherein the pulse conversion circuit includes a voltage control circuit which controls a bias voltage to the photoelectric conversion circuit, a pulse circuit converts the electrical signal outputted from the photoelectric conversion circuit into the electric pulse signal, and a coupling circuit which couples the pulse signal outputted from the pulse circuit to the voltage control circuit.

(4) The intraocular implant-type vision stimulating unit according to (3), wherein the pulse circuit includes an inverter or a Schmitt trigger whose input voltage is an output voltage of the photoelectric conversion circuit, and the coupling circuit connects a final output side of the pulse circuit and the voltage control circuit.

(5) The intraocular implant-type vision stimulating unit according to (4), wherein as the inverter or the Schmitt trigger of the pulse circuit, a plurality of inverters or Schmitt triggers are connected in series in an odd number.

(6) The intraocular implant-type vision stimulating unit according to (3), wherein the voltage control circuit includes transistors for switching which are respectively connected to a bias power supply of the power supply circuit, the photoelectric conversion circuit, and the coupling circuit.

(7) The intraocular implant-type vision stimulating unit according to (4), wherein the voltage control circuit includes a resistor inserted in series between the photoelectric conversion circuit and the coupling circuit, and a capacitor inserted in parallel with the photoelectric conversion circuit.

(8) The intraocular implant-type vision stimulating unit according to (7), wherein the resistor includes a transistor whose resistance value is variable.

(9) The intraocular implant-type vision stimulating unit according to (1), wherein the waveform shaping circuit includes a differentiating circuit which outputs the pulse signal outputted from the pulse conversion circuit as a pulse signal having a differential waveform.

(10) The intraocular implant-type vision stimulating unit according to (9), wherein the differentiating circuit includes a resistor and a capacitor.

(11) The intraocular implant-type vision stimulating unit according to (10), wherein the resistor includes a transistor whose resistance value is variable.

(12) The intraocular implant-type vision stimulating unit according to (1), wherein the power supply circuit includes at least one of a circuit which supplies electric power from a wiring physically connected to an outside, a circuit which supplies electric power by making use of electromagnetic waves from the outside, and a circuit which supplies electric power by generating electricity by the heat of a human body.

(13) The intraocular implant-type vision stimulating unit according to (1), wherein the pulse conversion circuit includes a frequency modulation circuit which sets the frequency of the pulse signal to a substantially fixed level when the magnitude of the electrical signal outputted from the photoelectric conversion circuit is not more than a first reference value or not less than a second reference value greater than the first reference value, and varies the frequency of the pulse signal in correspondence with the magnitude of the electrical signal when the magnitude of the electrical signal is not less than the first reference value and not more than the second reference value.

(14) The intraocular implant-type vision stimulating unit according to (13), wherein the pulse conversion circuit further includes an amplitude modulation circuit which varies an amplitude of the pulse signal in correspondence with the magnitude of the electrical signal when the magnitude of the electrical signal outputted from the photoelectric conversion circuit is not more than the first reference value or not less than the second reference value, and sets the amplitude of the pulse signal to a substantially fixed level when the magnitude of the electrical signal is not less than the first reference value and not more than the second reference value.

(15) The intraocular implant-type vision stimulating unit according to (13), wherein the frequency modulation circuit includes a voltage control circuit which controls a bias voltage to the photoelectric conversion circuit, an odd number of inverters or Schmitt triggers whose input voltage is an output voltage of the photoelectric conversion circuit, and a coupling circuit which couples the pulse signal outputted from the inverter or the Schmitt trigger to the voltage control circuit, and is arranged to set a lower limit frequency by regulating a charging leak source and a discharging leak source with respect to the photoelectric conversion circuit, and to set an upper limit frequency by providing a frequency filter before or after the inverter or the Schmitt trigger.

(16) The intraocular implant-type vision stimulating unit according to (1), further comprising:
a wave form memory which stores a predetermined electrical stimulation waveform; and
a timing control circuit which reads the electrical stimulation waveform from the waveform memory by obtaining an output of the pulse signal from the pulse conversion circuit.

(17) An intraocular implant-type vision stimulating unit for artificially generating the vision or a portion of the vision, comprising:
a photoelectric conversion circuit which converts incoming light into an electrical signal;
a pulse shaping circuit which shapes the electrical signal outputted from the photoelectric conversion circuit into an electric pulse signal corresponding to a magnitude of the electrical signal; and
a power supply circuit which supplies electric power to each of the circuits,
wherein the pulse signal is imparted to a retinal region through an electrode.

(18) The intraocular implant-type vision stimulating unit according to (17), wherein the pulse shaping circuit includes a circuit which modulates an amplitude of the pulse signal of a predetermined frequency into an amplitude corresponding to the magnitude of the electrical signal outputted from the photoelectric conversion circuit.

(19) The intraocular implant-type vision stimulating unit according to (18), wherein the pulse shaping circuit includes a circuit which modulates the pulse signal into a bipolar pulse signal in which absolute values of the amplitude are identical but polarities of the amplitude are opposite.

(20) The intraocular implant-type vision stimulating unit according to (17), wherein the pulse shaping circuit includes a circuit which changes the number of pulse signals of a predetermined frequency in a predetermined time duration in correspondence with the magnitude of the electrical signal outputted from the photoelectric conversion circuit.

BRIEF DESCRIPTION OF THE DRAWINGS

FIG. 2 is a schematic diagram of a pulse signal output;

FIG. 13 is a diagram illustrating a pulse amplitude modulation system in accordance with a fifth embodiment;

FIG. 17 is a diagram illustrating the operational timing in accordance with the sixth embodiment.

BEST MODE FOR CARRYING OUT THE INVENTION

Hereafter, a description will be given of the embodiments of the invention with reference to the drawings.

(First Embodiment)

Figure 1:
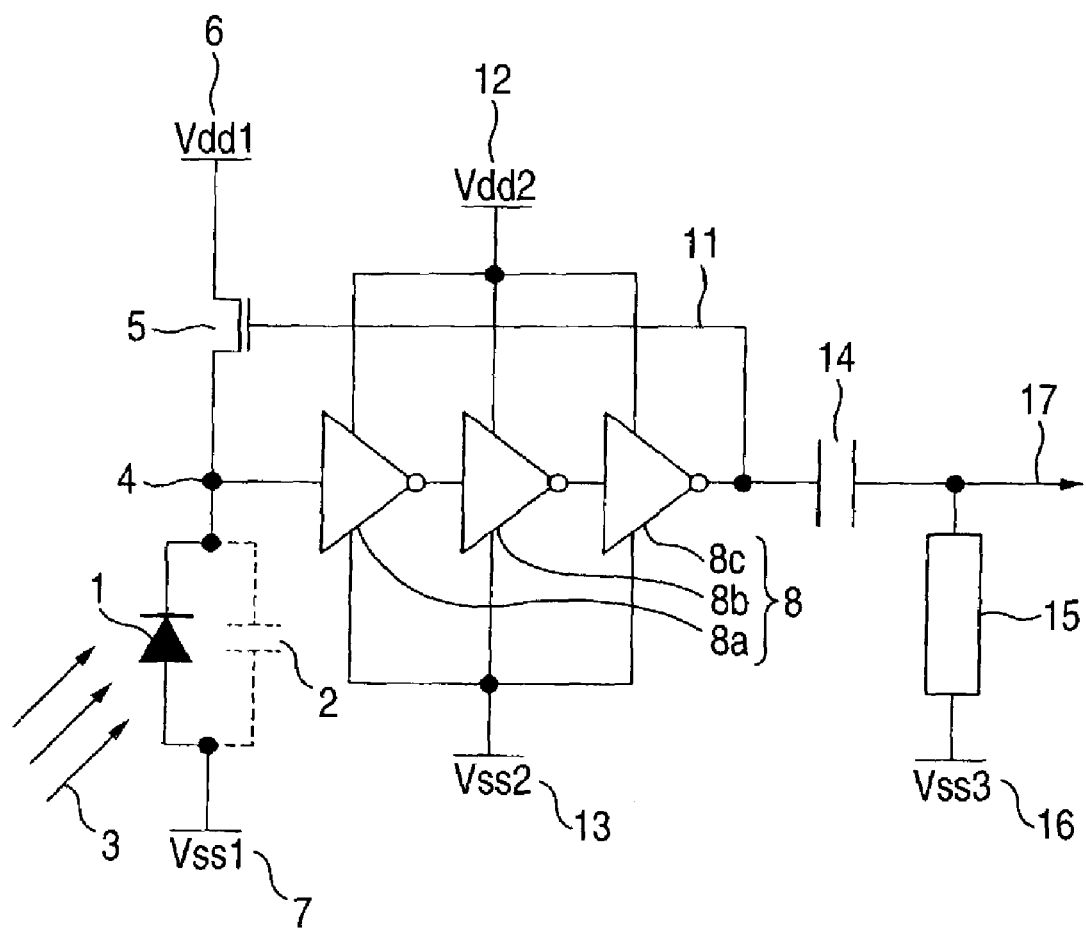
FIG. 1 is a schematic circuit diagram of a vision stimulating unit in accordance with a first embodiment.

FIG. 1 is a schematic circuit diagram of a vision stimulating unit in accordance with a first embodiment. Reference numeral 1 denotes a photodiode for converting the received light into an electric signal and outputting it; 2, a parasitic capacitance of the photodiode; 4, an n side of the photodiode; and 7, a p-side power supply for the photodiode. Numeral 5 denotes a reset transistor for controlling a bias voltage to the photodiode 1, and numeral 6 denotes a bias power supply for the reset transistor. Numeral 8 denotes an inverter row whose input voltage is the output voltage of the photodiode 1, and in which embodiment three inverters 8a, 8b, and 8c are connected in series in an odd number. Numeral 11 denotes a feedback path for connecting an output side of the inverter 8c and the reset transistor 5. Numeral 12 denotes a positive power supply for the inverter row, and numeral 13 denotes a negative power supply for the inverter row. Numeral 14 denotes a capacitor for a differentiating circuit, and numeral 15 denotes a resistor for the differentiating circuit, and numeral 16 denotes a negative power supply for the differentiating circuit. A pixel circuit 50 is formed by elements excluding the power supplies 6, 7, 12, 13, and 16, and is preferably configured as an integrated circuit. Numeral 17 denotes an output terminal (electrode) which is brought into contact with a retinal region.

Next, a description will be given of an output of a pulse signal in the circuit configuration in accordance with the first embodiment. In an initial state, the potential at the photodiode n side 4 is assumed to be at the ground potential. Accordingly, since the input potential at the inverter 8a becomes low, the output potential at the inverter 8a becomes high. Since the inverters are three stages of 8a, 8b, and 8c, the output potential at the inverter 8c also becomes high. Accordingly, the reset transistor 5 is turned on after a delay time of the inverter row 8. At this time, charging is started in the parasitic capacitance 2 by the power supply 6 through the reset transistor 5. When the potential at the photodiode 1 reaches a threshold voltage Vinv of the inverter 8a, the output potential at the inverter 8a is inverted from high to low, and the output potential at the inverter 8c is also inverted from high to low. The reset transistor 5 is consequently turned off after the delay time of the inverter row 8, and the charging stops. This charging voltage is discharged by a photoelectric current generated in the photodiode 1 by incoming light 3. As the threshold voltage Vinv of the inverter 8a is reached again, and the output voltage at the inverter 8a is inverted from low to high, the output potential at the inverter 8c is also inverted from low to high. The reset transistor 5 is consequently turned on, and charging is started again in the parasitic capacitance 2.

As the above-described operation is repeated, the output potential at the inverter row 8 repeats high and low states. Namely, an electric pulse signal is outputted. The frequency f of the pulse signal at this time is approximately expressed by the following formula:

$$f = I_{ph}/C_{PD}(V_{dd1} - V_{th} - V_{inv})$$

Here, CPD indicates a capacitance value of the parasitic capacitance 2, Vdd1 indicates the voltage of the power supply 6, Vth indicates the threshold voltage of the reset transistor 5, Vinv indicates the threshold voltage of the inverter 8a, and Iph indicates the photoelectric current of the photodiode 1. This pulse signal is differentiated by a differentiating circuit consisting of the capacitor 14 and the resistor 15, is converted into a positive/negative bipolar pulse signal and is outputted from the output terminal 17. Here, if it is assumed that the capacitance value of the capacitor 14 is Cd and that the resistance value of the resistor 15 is Rd, it is possible to obtain a differential waveform if the width td of the pulse signal outputted from the inverter row 8 is td>RdCd. It should be noted that the width td is basically the delay time of the inverter row 8 or thereabouts.

FIG. 2 is a schematic diagram of the pulse signal output obtained in the above-described manner. FIG. 2(a) shows fluctuations of the potential at the photodiode n side 4, FIG. 2(b) shows the pulse signal outputted from the inverter 8c, and FIG. 2(c) shows the positive/negative bipolar pulse signal converted by and outputted from the differentiating circuit. At in FIG. 2(a) indicates the delay time based on the inverter row 8, and by using the threshold voltage Vinv of the inverter 8a as a reference, the pulse signal outputted after that delay time Δt is inverted. This delay time Δt is dependent on the number of inverters connected in series in an odd number. In addition, the inclination of the decline of the potential at the photodiode n side 4 is dependent on the magnitude of the electric signal outputted from the photodiode 1. Namely, if the incoming light 3 is strong (the quantity of incoming light is large) and the quantity of light received by the photodiode 1 is large, the inclination of the decline of the potential at the photodiode n side 4 becomes sharp, and the period of the outputted pulse signal becomes short.

In this embodiment, an NMOSFET is used as the reset transistor 5, but it suffices insofar as the reset transistor 5 is a device or a circuit having a switching function. For example, a PMOSFET maybe used. Further, a combination of these, e.g., a transmission gate, maybe used. Furthermore, a bipolar transistor or other transistor may be used.

In addition, Schmitt triggers may be used instead of the respective inverters 8a, 8b, and 8c.

Figure 3:
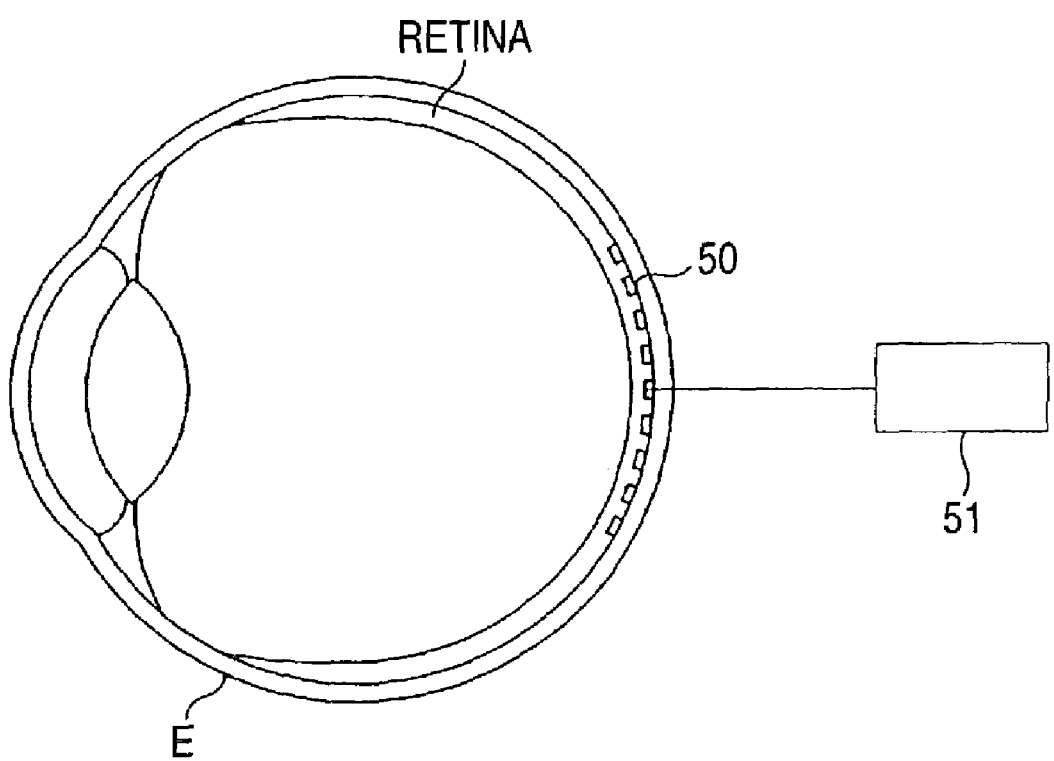
FIG. 3 is a diagram of implanting and disposition of the vision stimulating unit in the eye.

FIG. 3 is a diagram of implanting and disposition in the eye of the vision stimulating unit including the above-described pixel circuits 50. A multiplicity of pixel circuits 50 are implanted in the form of a two-dimensional array beneath the retina of a patient's eye (between a pigment epithelium layer and a neuroepithelial layer of the retina, or between the ganglionic layer of optic nerve and a neuroepithelial layer of retina). Reference numeral 51 denotes a power supply circuit for supplying electric power to the respective pixel circuits 50, and the power supply circuit 51 includes the power supplies 6, 7, 12, 13, and 16. As the power supply circuit 51, a system using electromagnetic waves from the outside may be used in addition to the system for supplying electric power to the respective pixel circuits 50 from the wiring physically connected to the outside. For example, a voltage is generated by sending electromagnetic waves to coils attached to the respective pixel circuits 50 from a coil of eyeglasses fitted outside the eyeball.

In addition, as the power supply circuit 51, it is also possible to use a system based on electric generation from the heat of the human body. Thermoelectric generation can be arranged for by a unit using the "Seebeck effect" in which a voltage occurs if a temperature difference is given, e.g., a unit in which p-type bismuth-tellurium and n-type bismuth-tellurium are formed into a pn junction. The regulation of the voltage which is outputted can be made possible by connecting a number of combinations of the pn junctions in series. In a case where such a thermoelectric generator unit is implanted in a human body, the unit is disposed at a portion where heat escapes by blood flow. Electric generation based on the heat of the human body is able to avoid the effect (such as heat generation) of electromagnetic waves on the human body.

Thus, by using as the electric supply circuit the system for supplying electric power from the wiring physically connected to the outside, the system making use of electromagnetic waves from the outside, or the system based on electric generation from the heat of the human body, it becomes unnecessary to implant a primary battery into the human body. Hence, it is possible to avoid the effect of the replacement of the primary battery on the human body. In addition, a secondary battery may be implanted and connected to the power supply circuit 51 to attain improvement of the driving of the circuit.

In the circuit having the above-described configuration, photoelectric conversion is made possible in a digital output form in which the electric pulse signal is outputted at a frequency corresponding to the quantity of the incoming light 3. In addition, the positive/negative bipolar pulse signal can be outputted even at a low voltage of 1 V or less and with a very small quantity of incoming light. Accordingly, even a very small photodiode in a narrow region beneath the retina is capable of stimulating retinal cells. In addition, if the position where the pixel circuits 50 are implanted is the subretinal region, the retinal cells can be efficiently stimulated by the outputted pulse signals, variance between image information from the outer world and vision information is difficult to occur.

In addition, by controlling the supply voltage of each circuit provided in the pixel circuit 50 by the power supply circuit 51, it is possible to vary pulse characteristic parameters, such as the period and width of the pulse signal which is outputted, the bipolar pulse shape, and the bipolar pulse intervals.

In addition, the above-described circuit configuration is formed by standard and simple circuits, and the circuitry can be configured by passive components alone.

In addition, since the differentiating circuit for converting the signal into the positive/negative bipolar pulse signal and for outputting the same is inserted after the inverter row 8, the bipolar pulse signal can be outputted by a single photodiode and small-size circuits.

It should be noted that, as a method of amplifying the signal, a system using a charge-coupled type CCD is known, but this system requires a timing signal (clock) for outputting after the accumulation. For this reason, the wiring from each timing circuit is required for each device. In contrast, timing is unnecessary with the above-described pixel circuit, so that the circuit wiring and the circuit configuration are made extremely simple.

(Second Embodiment)

Figure 4:
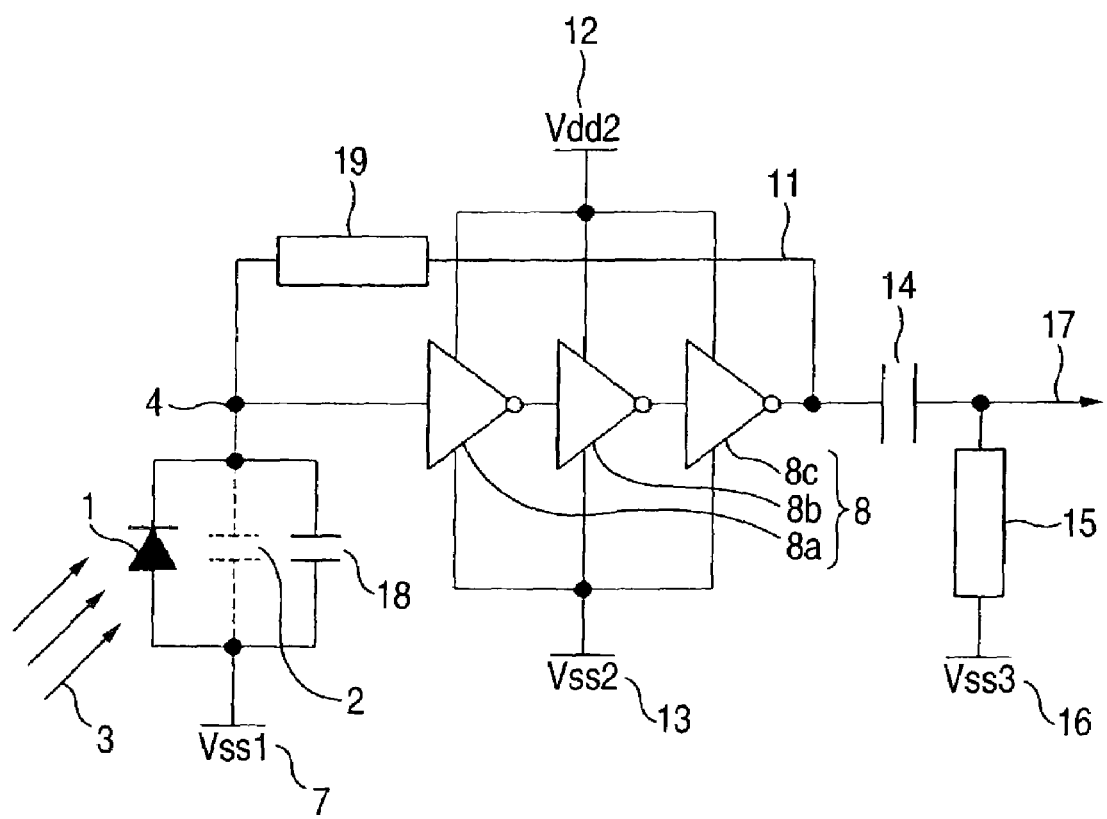
FIG. 4 is a schematic circuit diagram of the vision stimulating unit in accordance with a second embodiment.
Figure 5:
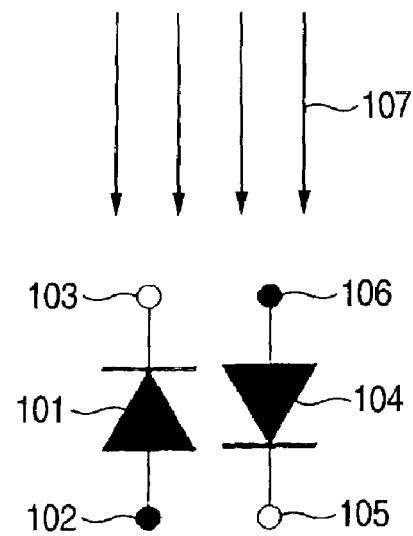
FIG. 5 is a schematic circuit diagram of a conventional intraocular implant-type vision stimulating unit.

FIG. 4 is a schematic circuit diagram of the vision stimulating unit in accordance with a second embodiment. It should be noted that those elements that are identical to those of the first embodiment are denoted by the same reference numerals. Here, unlike the first embodiment, a capacitor 18 is inserted in parallel with the photodiode 1. In addition, a resistor 19 is inserted in the feedback path 11. The output voltage at the inverter 8c also serves as a bias power supply for the photodiode 1. An integrating circuit is formed by the capacitor 18 and the resistor 19. Further, since the photodiode 1 is parallel to the capacitor 18, the photoelectric current of the photodiode 1 affects the time constant of this integrating circuit. Namely, if the incoming light 3 is strong (if the quantity of incoming light is large), the capacitor 18 is discharged more speedily, and the time constant becomes correspondingly shorter, so that the period of the pulse signal which is outputted becomes short. In the case of this embodiment, since the reset transistor 5 in the first embodiment is not provided, the pulse signal is outputted without dependence on the driving capability of the reset transistor 5. If the driving capability is low, the state becomes such that the charging and discharging of the photodiode 1 counteract with each other, the width of the pulse signal becomes wide and the upper limit of the frequency becomes low, resulting in a decrease in the dynamic range decreases (conversely, there is an advantage in that the dynamic range can be altered). The circuit configuration of this embodiment is free of that limitation. In addition, in the circuit configuration of this embodiment as well, the circuitry can be configured by passive components alone.

It should be noted that, as for the resistor 19, a transistor may be used. In the case where the transistor is used, since an ordinary logic process can be applied without requiring a special resistor fabrication program, the integration density can be increased by using the latest miniaturization process, thereby making it possible to attain a compact size and low power consumption. Alternatively, if a general-purpose process is used, low cost can be attained.

In addition, in the vision stimulating unit of this embodiment, as the gate potential at the transistor used as the resistor 19 is controlled by the power supply circuit 51 to vary a resistance value, it is possible to vary the period and width of the pulse signal. Therefore, it is possible to stimulate by flexibly coping with the condition of the retina.

It should be noted that although, in the above-described first and second embodiments, no particular description has been given of the photodiode 1, it suffices if the photodiode 1 has a structure capable of efficiently effecting photoelectric conversion, such as a pn junction type photodiode, and this is not limited to the photodiode. It goes without saying that similar effects are offered by the use of, for example, a Group IV simple substance or a Group IV mixed crystal, a Group III–V simple substance or a Group III–V mixed crystal, or a Group II–V simple substance or a Group II–V mixed crystal of Si and SiGe or a combination thereof. In the case where the photodiode is not used, it suffices if a parasitic capacitance is intentionally inserted in parallel.

In addition, as for the differentiating circuit consisting of the capacitor 14 and the resistor 15, it suffices if it is capable of outputting only the rise and fall of the pulse signal waveform. For example, a transistor may be used as the resistor 15. Still alternatively, it is possible to use a combination with another differentiating circuit, e.g., an operational amplifier. By using a transistor as the resistor 15 and by varying its resistance value, it is possible to control pulse characteristic parameters such as the interval and amplitude of the bipolar pulse signal, and stimulation can be effected in correspondence with the condition of the retina. Consequently, more effective vision stimulation becomes possible. Furthermore, since the transistor is used, it is possible to apply a general-purpose logic process.

(Third Embodiment)

In the circuit configuration of a third embodiment, a pulse frequency modulation circuit, which is based on a pulse frequency modulation system for limiting upper and lower limits of the frequency of the outputted pulse signal, is added to the circuit configurations of the first and second embodiments. In the human vision, the flickering of a light source is generally perceived by the stimulation with a frequency of 30 Hz or below. In addition, by the stimulation with a frequency in excess of 1 to 10 kHz, there are possibilities that neurons are not properly stimulated (e.g., the possibility that an ionic current cannot transmit the high frequency signal, and the possibility that retinal neurons do not assume an excited state).

Figure 7:
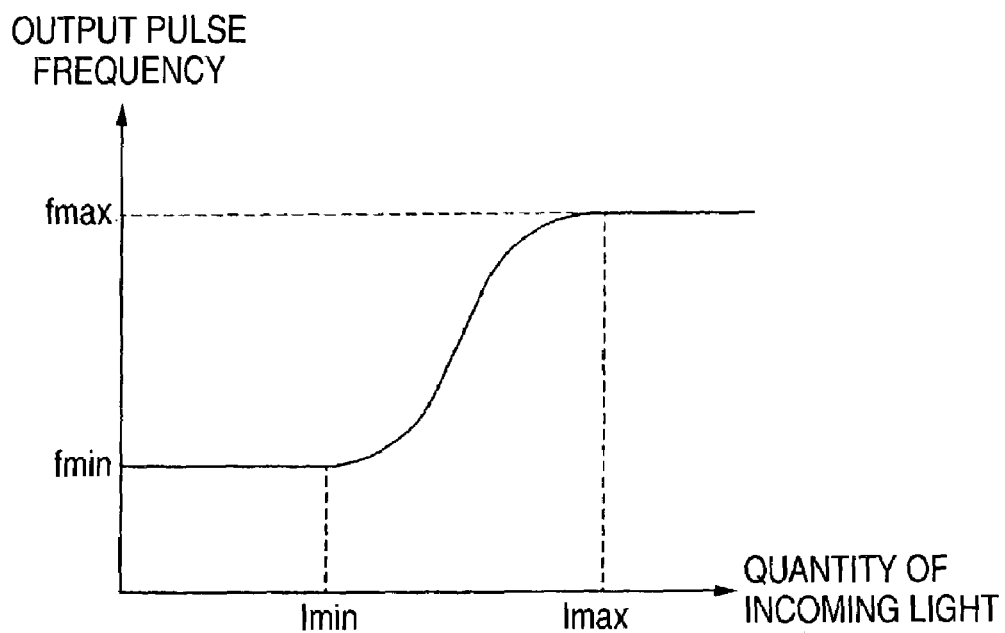
FIG. 7 is a diagram explaining a pulse frequency modulation system in accordance with the third embodiment.
Figure 7:
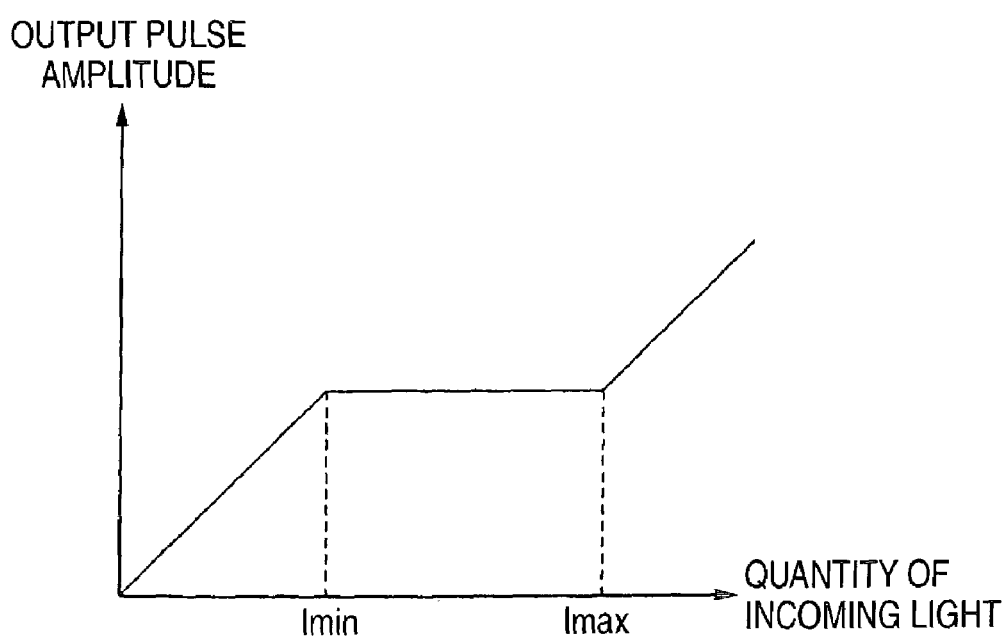

Accordingly, in this embodiment, an arrangement is provided such that an upper limit (fmax) and a lower limit (fmin) of the frequency of the pulse signal to be outputted can be restricted (set) (see FIG. 7($a$)). Further, in a region not less than the lower limit and not more than the upper limit, the amplitude of the pulse signal is kept substantially fixed, while in a region not more than the lower limit and not less than the upper limit, the amplitude is increased in correspondence with an increase in the quantity of incoming light (see FIG. 7($b$)) By virtue of such a pulse frequency modulation system it is possible to output a pulse signal fitted to a wide range of the quantity of light.

Figure 6:
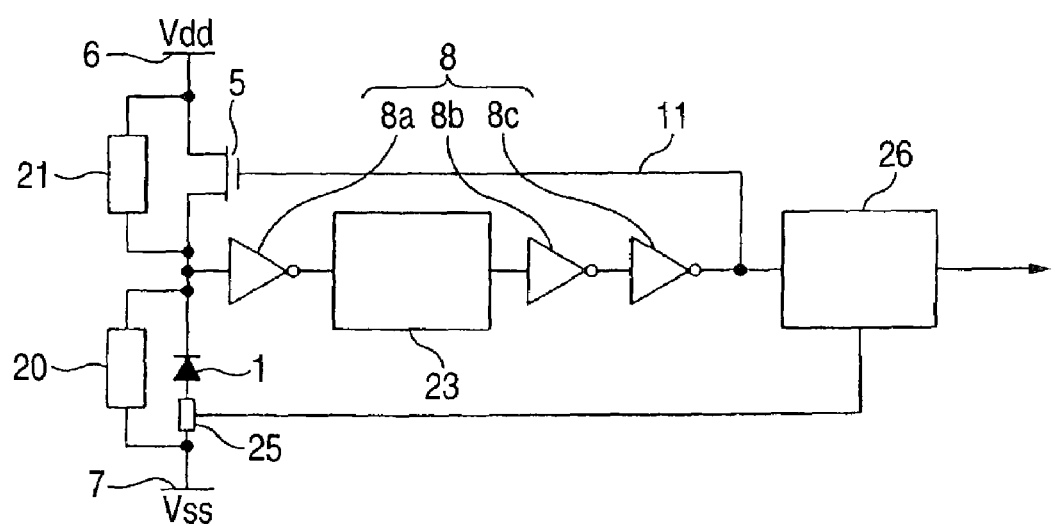
FIG. 6 is a schematic circuit diagram of the vision stimulating unit in accordance with a third embodiment.

FIG. 6 is a schematic circuit diagram of the vision stimulating unit in accordance with the third embodiment. It should be noted that those elements that are identical to those of the first embodiment are denoted by the same reference numerals. As the potential charged in the photodiode 1 is forcibly discharged by a discharging leak source 20, the cathode potential of the photodiode 1 is caused to drop, and the pulse signal is outputted. Consequently, the pulse signal can be outputted at a lower limit frequency even in a case where the incoming light is weak (the quantity of incoming light is small) (in the case of not more than a reference value Imin). In addition, a dark current flows across the photodiode 1. For this reason, even in cases where there is no incoming light, the cathode potential of the photodiode 1 drops, and the pulse signal is outputted. It should be noted that even in cases where the dark current is large or there is not incoming light, there is a possibility of the lower limit frequency or the upper limit frequency being exceeded. To prevent this phenomenon, a charging leak source 21 is provided for the purpose of compensating for the dark current.

To restrict the upper limit of the frequency, a frequency filter 23 is provided in the inverter row 8. The position of the frequency filter 23 is sufficient if it is located before or after any one of the inverters. In FIG. 6, the frequency filter 23 is provided between the inverters 8$a$ and 8$b$. When the incoming light is strong (in the case of not less than a reference value Imax), and even if the cathode potential at the photodiode 1 drops sharply, a change at a cut-off frequency or higher is cut off. Hence, the upper limit of the frequency of the outputted pulse signal becomes the cut-off frequency of the frequency filter 23.

In the case where the amplitude of the outputted pulse signal is fixed, the stimulus intensity becomes fixed at the upper limit or higher, and the quantity of incoming light ceases to be reflected on the stimulus intensity. To allow the quantity of incoming light to be reflected on the pulse signal which is outputted at not more than the lower limit and not less than the upper limit of the frequency, the photoelectric current of the photodiode 1 is detected in these regions by a photoelectric current detection circuit 25. Further, the amplitude of the pulse signal which is outputted is modulated by an amplitude modulation circuit 26 provided after the inverter row 8 in correspondence with the detected amount of photoelectric current.

As shown in FIG. 7($b$), at the lower limit frequency (fmin) or above and at the upper limit frequency (fmax) or below, the amplitude modulation circuit 26 sets the amplitude of the pulse signal which is outputted to a fixed level. At the lower limit frequency (fmin) or below and at the upper limit frequency (fmax) or above, the amplitude modulation circuit 26 monotonously increases the amplitude of the pulse signal which is outputted in correspondence with the quantity of incoming light. To realize this, the photoelectric current detection circuit 25 is provided on one side of the photodiode 1, and the amplitude of the pulse signal which is outputted is modulated by the amplitude modulation circuit 26 in correspondence with the detected quantity of incoming light.

Figure 8:
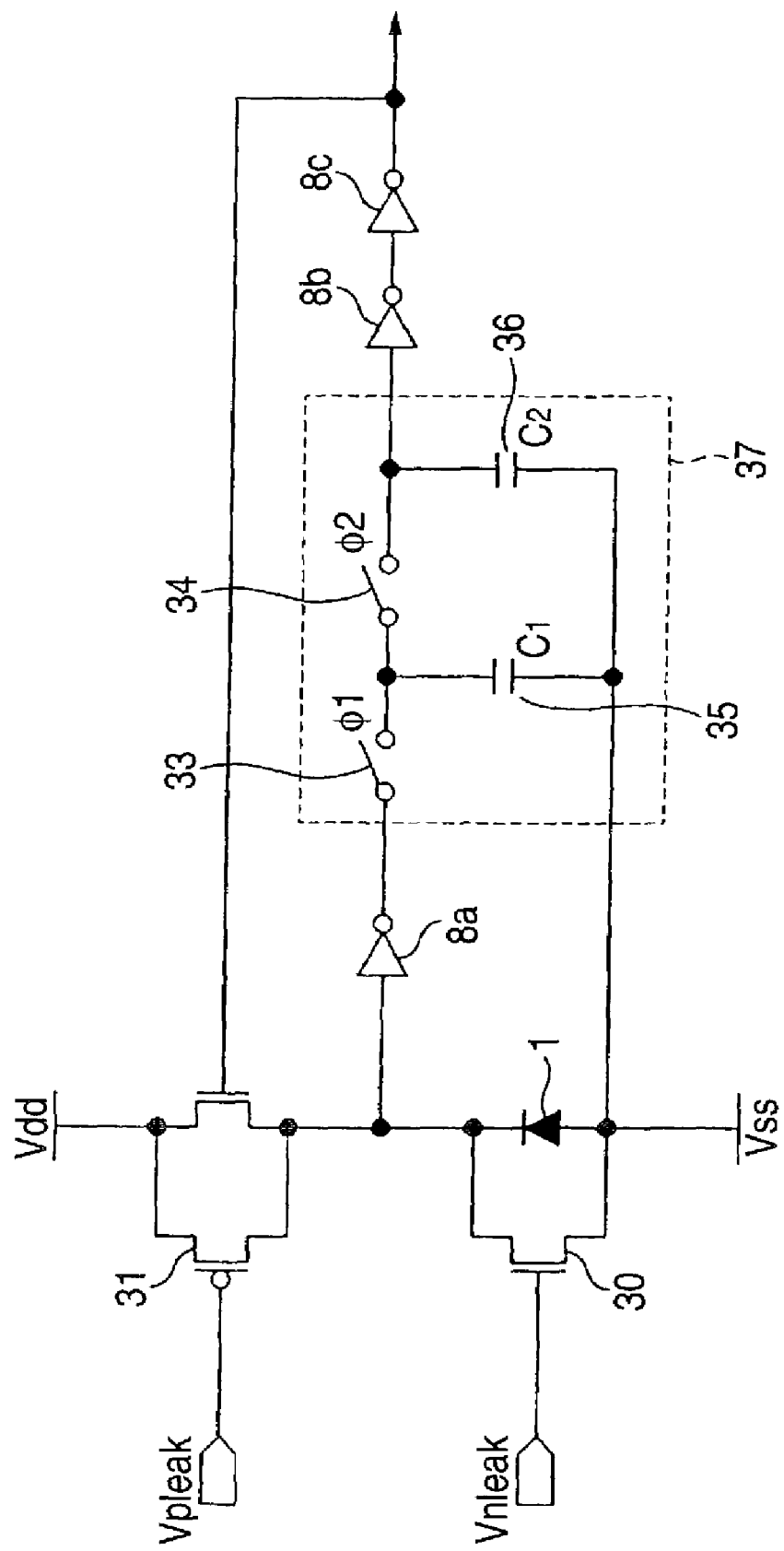
FIG. 8 is a schematic circuit diagram of the vision stimulating unit including a pulse frequency modulation circuit in accordance with the third embodiment.
Figure 9:
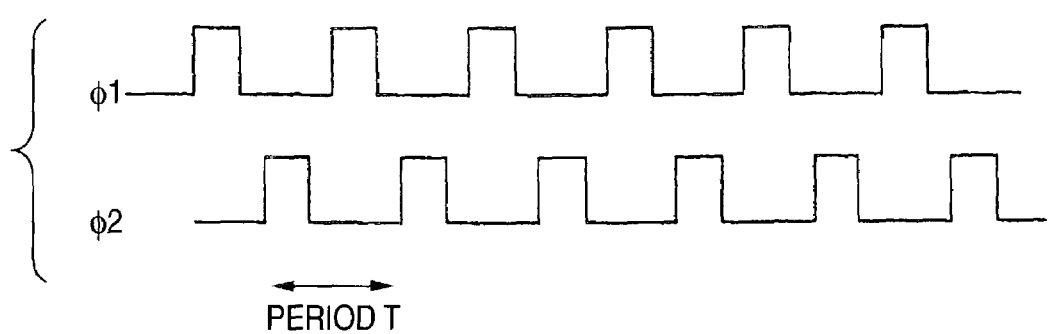
FIG. 9 is a diagram illustrating the timing for opening or closing two transmission gates shown in FIG. 8.

FIG. 8 is a schematic circuit diagram of the vision stimulating unit including the pulse frequency modulation circuit for restricting the frequency of the pulse signal which is outputted. It should be noted that in this drawing the amplitude modulation circuit for modulating the amplitude of the pulse signal which is outputted in correspondence with the quantity of incoming light is not included. In this example, a PMOS transistor 31 is used as the charging leak source, and an NMOS transistor 30 is used as the discharging leak source. In addition, a switched capacitor filter 37 consisting of two transmission gates 33 and 34 and two capacitors 35 and 36 is used as the frequency filter 23. A low-pass filter is constructed by opening or closing the transmission gates 33 and 34 at timings shown in FIG. 9. Clocks Φ1 and Φ2 of the transmission gates 33 and 34 may be generated by oscillators provided in the pixel circuits, or may be generated by an oscillator provided outside the pixel circuits in common thereto.

Here, if it is assumed that the charge accumulated in the capacitor 35 is C1, the charge accumulated in the capacitor 36 is C2, and the period of the clocks Φ1 and Φ2 imparted to the transmission gates 33 and 34 is T, the cut-off frequency is expressed by (C2/C1)/T. This becomes the upper limit frequency (fmax) of the pulse signal which is outputted. By adjusting potentials Vpleak and Vnleak which are respectively applied to the transistors 30 and 31, the leak current is adjusted, and the lower limit frequency (fmin) is set. The amplitude of the pulse signal which is outputted is set to be slightly lower than the threshold at which retinal cells are stimulated in the lower limit frequency.

(Fourth Embodiment)

Figure 10:
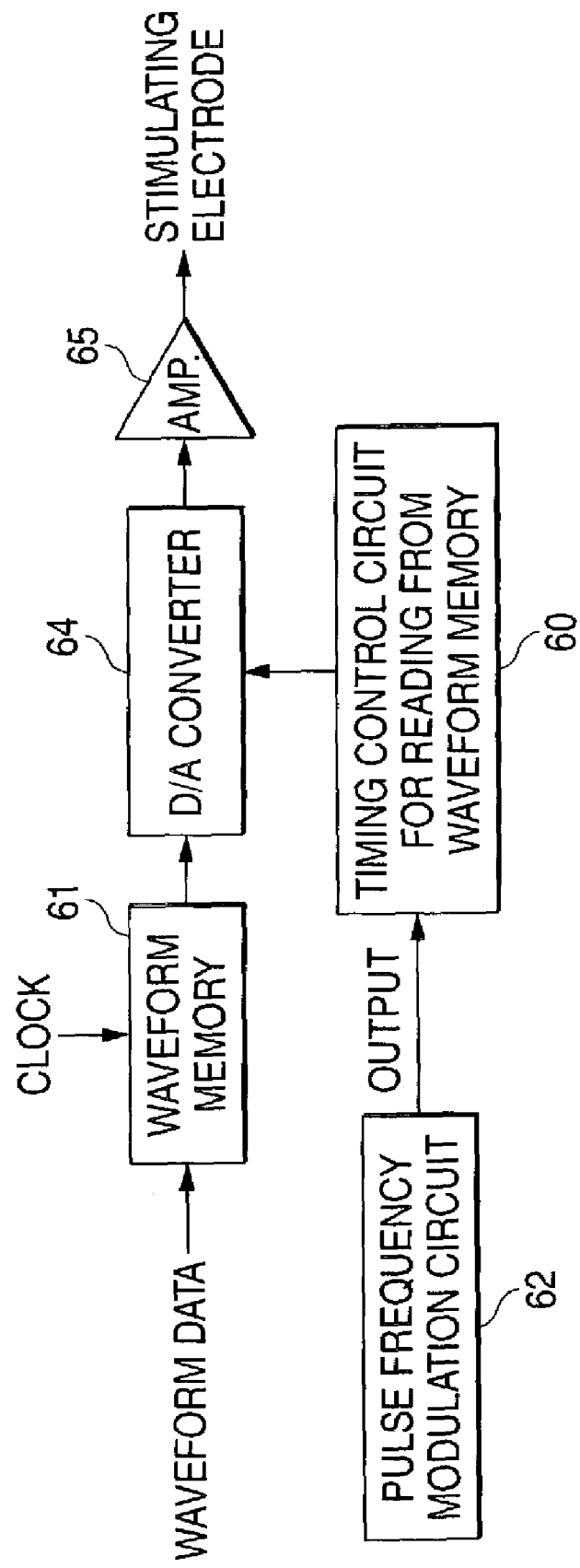
FIG. 10 is a schematic block diagram of a waveform shaping circuit in accordance with a fourth embodiment.

In the circuit configuration of the vision stimulating unit in accordance with a fourth embodiment, a programmable waveform shaping circuit is added. A circuit for generating an electrical stimulation waveform of an arbitrary shape is added after the pulse frequency modulation circuit of the third embodiment or the like, so as to output a pulse signal of an optimal waveform for cell stimulation. FIG. 10 is a schematic block diagram of the waveform shaping circuit.

The shapes of the waveform for stimulating neurons include various shapes such as unipolar waveform, bipolar waveform, sawtooth waveform, and bipolar sawtooth waveform, but bipolar shapes are preferable. The waveform data is stored in a waveform memory 61. The waveform memory 61 may be an analog memory or a digital memory, but the case of the digital memory is shown in FIG. 10. This circuit outputs once the waveform stored in the waveform memory 61 by being controlled by a timing control circuit 60 for reading from the waveform memory, when a pulse signal is outputted from a pulse frequency modulation circuit 62. The outputted waveform is outputted to an output terminal (electrode) through a D/A converter 64 and an amplifier 65.

Figure 11:
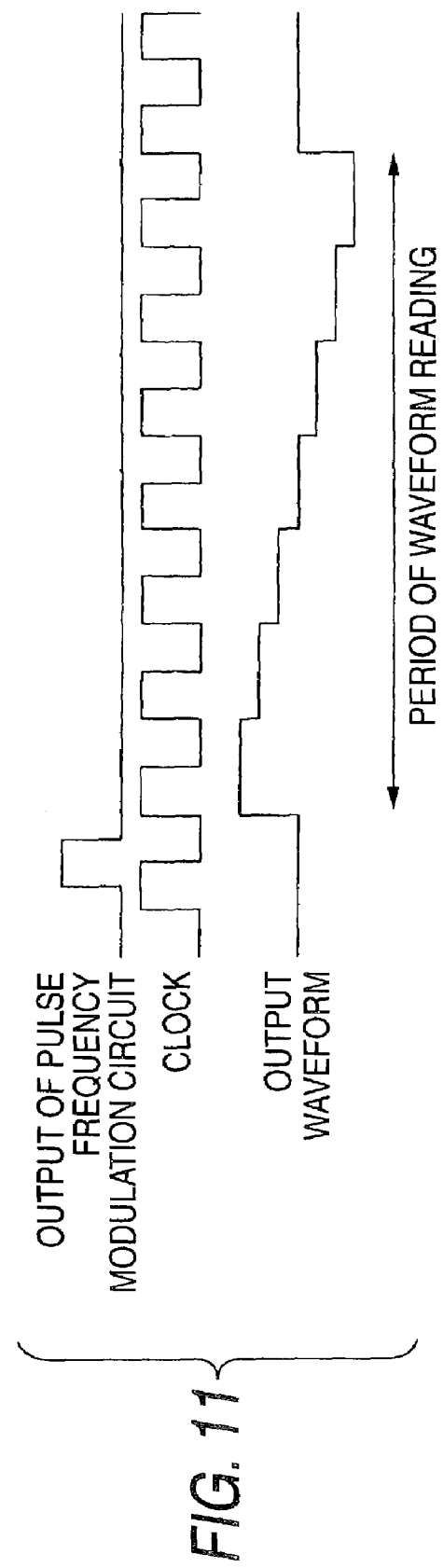
FIG. 11 is a diagram illustrating the waveform outputted from the waveform shaping circuit in accordance with the fourth embodiment.

FIG. 11 is a diagram illustrating the waveform which is outputted from the waveform memory 61. Here, a state is shown in which a bipolar sawtooth waveform is being outputted. If the pulse signal output is given once from the pulse frequency modulation circuit 62, the bipolar sawtooth waveform is outputted at the timing of the clock from the oscillator only during the period of waveform reading by the timing control circuit 60.

Figure 12:
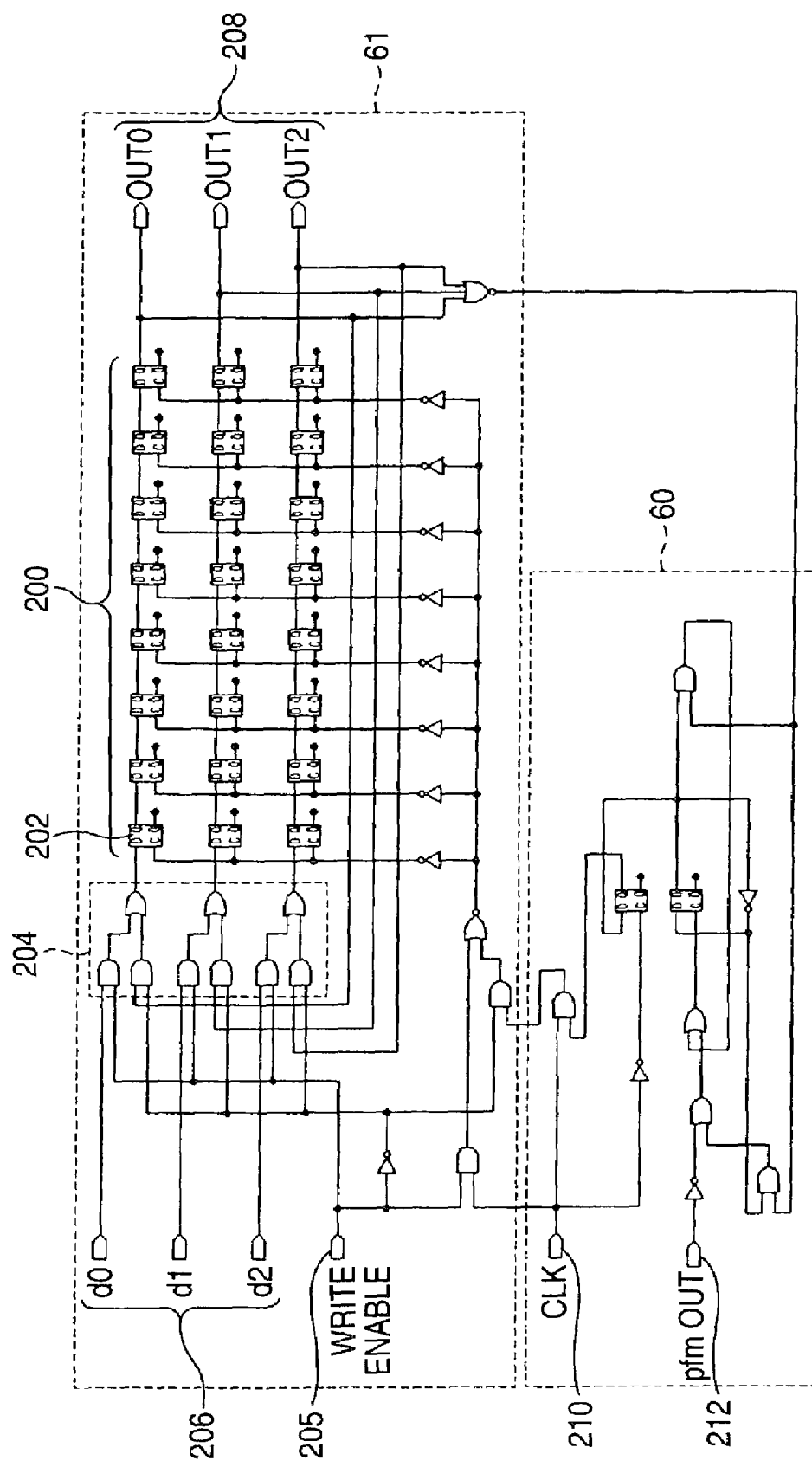
FIG. 12 is a schematic circuit diagram of a waveform memory and a timing control circuit in accordance with the fourth embodiment.

FIG. 12 is a schematic circuit diagram of the waveform memory 61 and the timing control circuit 60 for reading from the waveform memory in this programmable waveform shaping circuit.

A memory 200 consists of D flip-flops 202 in 3 rows×8 columns, and the waveform data is stored in the D flip-flops 202. The memory 200 constitutes a shift register, and the output of the shift register is fed back to an input-side selector circuit 204. The memory 200 has a capacity of 8 words (1 word, 3 bits), and the amplitude of the pulse signal can be set in seven stages. Digital signals are inputted from three input terminals (d0, d1, and d2) 206 after a write enable terminal 205 is set to high, thereby making it possible to input the waveform to the memory 200 in synchronism with the clock signal inputted to a clock terminal 210. If the pulse signal outputted from the pulse frequency modulation circuit 62 is inputted after the write enable terminal 205 is set to low, the pulse signal of an arbitrary waveform synchronized with the clock signal is outputted from output terminals 208. This outputted digital value is converted into an analog value by the D/A converter, and is outputted as a stimulation voltage. The timing control signal 60 consists of two D flip-flogs, AND circuits, and the like, and is designed to synchronize the clock signal and the pulse signal inputted from the pulse frequency modulation circuit 62 to a terminal 212.

All the 0 data are halt IDs for the shift register, and are added to ends of the data. At a point of time when all the output words in the shift register have becomes 0s, the shift is halted, and the state becomes such as to wait for an ensuing pulse signal from the pulse frequency modulation circuit 62. Since one halt ID is necessarily included, the circuit shown in FIG. 12 is actually a 7-word memory.

(Fifth Embodiment)

A fifth embodiment is an example of the vision stimulating unit for stimulating retinal cells by a pulse amplitude modulation system. In this unit, the amplitude of a pulse signal of a fixed frequency is modulated in correspondence with the quantity of incoming light. The pulse signal may be unipolar or bipolar, but is preferably bipolar. In the case of the unipolar pulse signal, the retinal cells are stimulated by the pulse signal of an amplitude corresponding to the quantity of incoming light. In the case of the bipolar pulse signal, the retinal cells are stimulated by the pulse signal in which absolute values of the amplitude are identical but polarities of the amplitude are opposite, following the pulse signal of the amplitude corresponding to the quantity of incoming light. The frequency of the pulse signal which is outputted is set to an appropriate frequency of such a measure as to allow the retinal cells to receive stimulus. The input of this unit is an output voltage or an output current of a photoelectric conversion circuit using such as an active pixel sensor or a phototransistor used in a CMOS image sensor.

FIG. 13 is a diagram explaining the pulse amplitude modulation system of the fifth embodiment. When the electrical signal (photoelectric conversion waveform) converted by a photoelectric conversion circuit is inputted as shown in FIG. 13(a), the electrical signal is subjected to sampling by sampling pulses shown in FIG. 13(b), and a pulse signal whose amplitude is modified as shown in FIG. 13(c) or 13(d) is outputted. FIG. 13(c) is an example of the output in the case of the unipolar pulse signal, and FIG. 13(d) is an example of the output in the case of the bipolar pulse signal.

Figure 14:
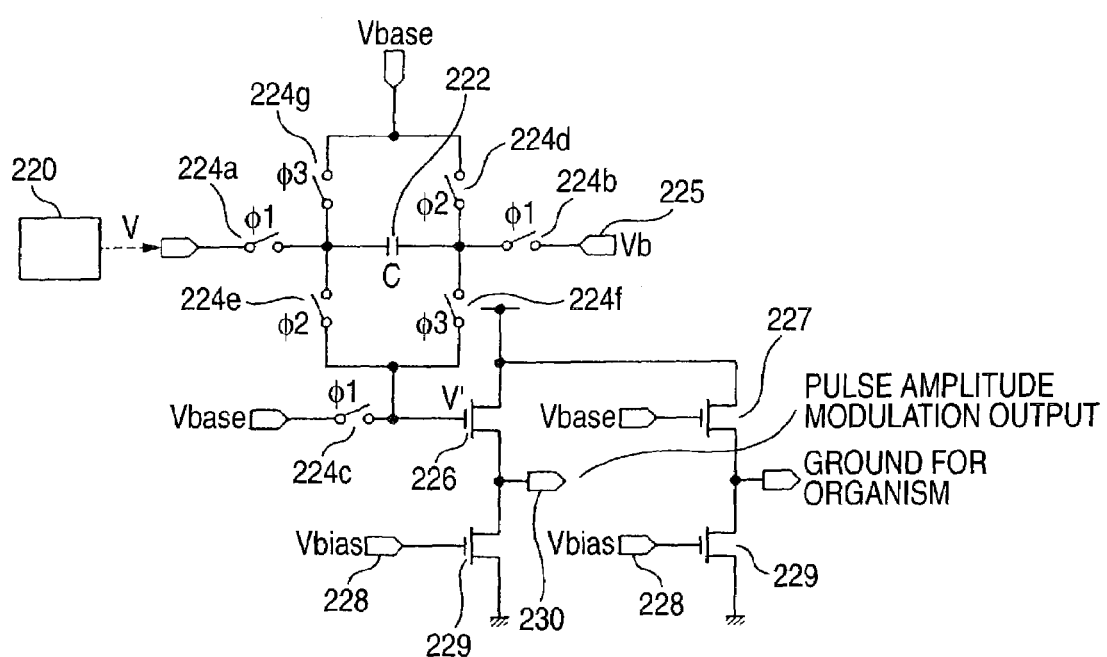
FIG. 14 is a schematic circuit diagram of a pulse generating circuit based on the pulse amplitude modulation system in accordance with the fifth embodiment.

FIG. 14 is a schematic circuit diagram of a pulse generating circuit based on the pulse frequency modulation system. A bipolar pulse signal is generated by a capacitor 222 and seven MOS switches 224a to 224g. Outputs of a photoelectric conversion circuit 220 are accumulated in the capacitor 222 at timings when the switches (Φ1) 224a, 224b, and 224c are closed. The outputs of the photoelectric conversion circuit 220 are assumed to be voltage signals. The potential difference accumulated in the capacitor 222 becomes the difference (V−Vb) between an output potential V of the photoelectric conversion circuit 220 and a potential Vb from a terminal 225. In a case where an increase in the voltage outputted from the photoelectric conversion circuit 220 and an increase in the quantity of incoming light are of the same sign, Vb from the terminal 225 is set to 0. On the other hand, in a case where they are of different signs, Vb from the terminal 225 is set to the power supply level. If Vb is set to 0, the output of the photoelectric conversion circuit 220 is stored as it is, whereas if VB is set to the power supply level, a value in which the output of the photoelectric conversion circuit 220 is inverted is stored. If the switches (Φ1) 224a, 224b, and 224c are closed in a state in which the switches (Φ1) 224*a*, 224*b*, and 224*c*, the switches (Φ2) 224*d* and 224*e*, and the switches (Φ3) 224*f* and 224*g* are initially open, an input voltage V' of a source follower 226 becomes Vbase.

Next, after the switches (Φ1) 224*a*, 224*b*, and 224*c* are opened, if the switches (Φ2) 224*d* and 224*e* are closed, $$V'=Vbase+V-Vb$$

After the switches (Φ2) 224*d* and 224*e* are opened, if the switches (Φ3) 224*f* and 224*g* are subsequently closed, $$V'=Vbase-(V-Vb)$$

Figure 15:
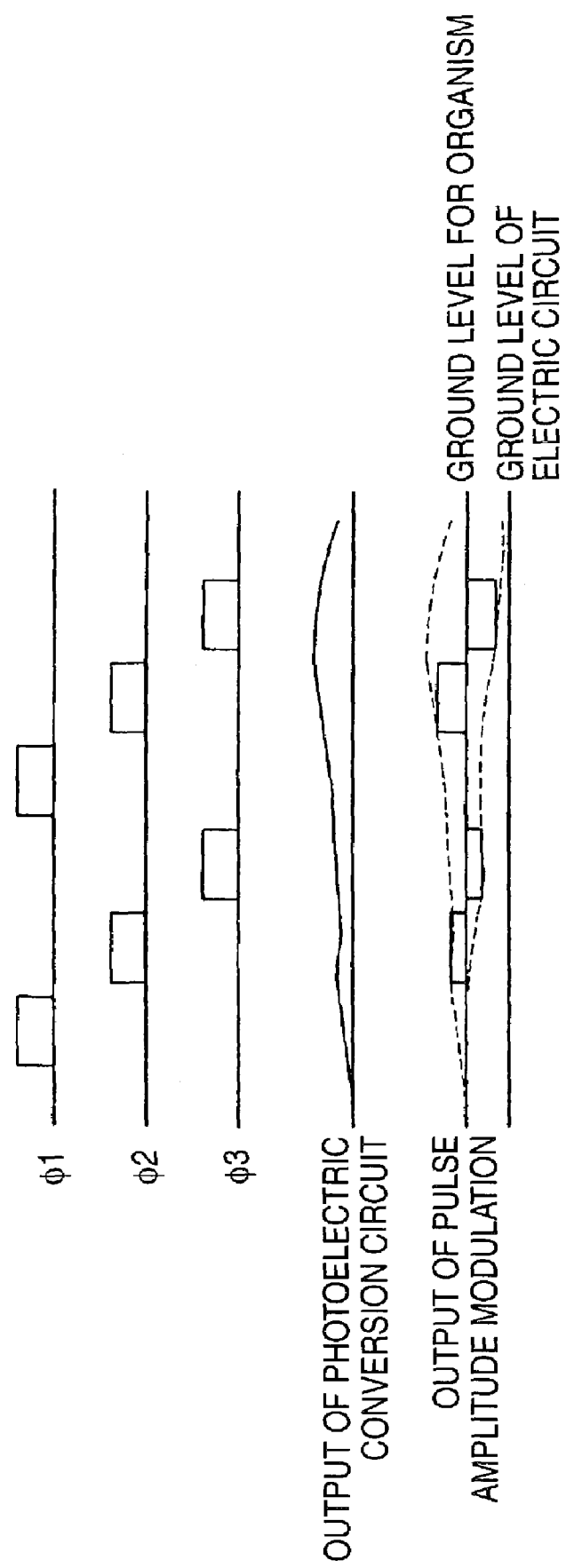
FIG. 15 is a diagram illustrating the relationship among sampling pulses due to the opening and closing of switches (Φ1), (Φ2), and (Φ3) shown in FIG. 14, an output of a photoelectric conversion circuit, and an output based on the pulse amplitude modulation.

By such a procedure, a bipolar pulse signal having an amplitude corresponding to the output of the photoelectric conversion circuit 220 is outputted from an output terminal 230. FIG. 15 shows the relationship among sampling pulses due to the opening and closing of the switches (Φ1), (Φ2), and (Φ3), the output of the photoelectric conversion circuit 220, and the output based on the pulse amplitude modulation. In this circuit, the base level of the bipolar pulse signal becomes higher than the ground level of the electronic circuits making up the pixel circuit. For this reason, the potential Vbase is outputted through a source follower 227 and is set as the organism side ground level to generate positive/negative bipolar pulse signals in the organism. As for Vbias to a terminal 228, an arbitrary voltage is inputted to allow a transistor 229 to perform the same operation as that of a resistor.

In this pulse amplitude modulation system, since the pulse signal is outputted at a fixed frequency, specific cells can be stimulated stably. In addition, retinal cells which are close to visual cells exhibiting analog-wise relaxation can be stimulated by analog signals.

(Sixth Embodiment)

A sixth embodiment is an example of the vision stimulating unit for stimulating retinal cells by a pulse-number modulation system. Here, the pulse-number modulation system refers to a system in which the frequency of the pulse signal is fixed, and the stimulation intensity is varied by the number of pulses included in a fixed time duration. For example, if the on state of the signal is assumed to be "1," and the off state "0," modulation is effected in the following manner:

| | |
|---|---|
| Weak light: | 101000000000 |
| Intermediate light: | 101010100000 |
| Strong light: | 101010101010 |

In the case where this system is adopted for retinal stimulation, a stimulation waveform (unipolar, bipolar, etc.) is outputted at the positions of "1s."

As advantages of using this system, it is possible to cite, among others, the following: (1) it is possible to reduce the effect of a change of a firing threshold caused by an electrical stimulation frequency in the retinal stimulation, (2) the electronic circuit configuration is simple, and (3) it is easy to design a circuit for controlling the stimulation waveform (such as a bipolar waveform having different peak values).

Figure 16:
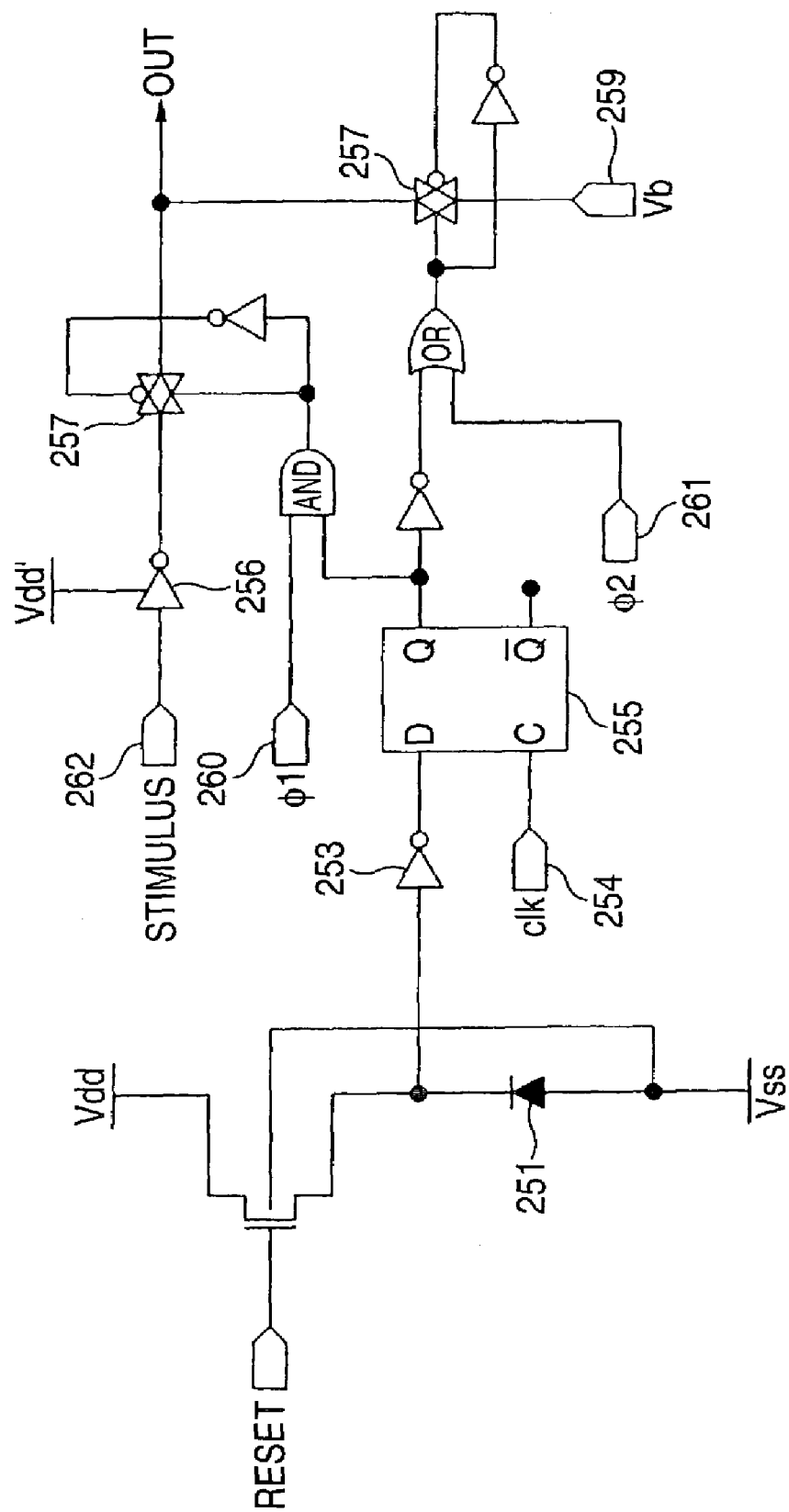
FIG. 16 is a schematic circuit diagram of a pulse generating circuit based on a pulse-number modulation system in accordance with a sixth embodiment.

FIG. 16 is a schematic circuit diagram of a pulse generating circuit based on the pulse-number modulation system, and FIG. 17 is a diagram illustrating its operational timing. In FIG. 16, a photodiode 251 is charged to the supply voltage during resetting. At this time, the output potential of an inverter 253 is set to low. Photoelectric charge is generated by the incoming light, and the cathode potential of the photodiode 251 drops. When the cathode potential has dropped below the threshold potential of the inverter 253, the output potential of the inverter 253 is inverted to high. The light intensity and the time from the reset until the output potential is inverted are proportional. To output the output waveform in an integral unit (to prevent a situation in which the waveform of one period is cut off midway and is outputted), the output of the inverter 253 is temporarily stored in a flip-flop 255 in synchronism with the clock signal from a clk terminal 254. In a case where the output potential of the flip-flop 255 is high, the stimulation waveform is outputted. In the drawing, a waveform shaping circuit using an analog switch (transmission gate or the like) 257 of an inverter 256 is used. As the supply potential of the inverter 256, a potential Vdd' is used which is from an arbitrarily changeable power supply 258 and which is separate from the supply potential to be imparted to other elements.

This circuit is capable of generating unipolar and bipolar pulse signals, and is capable of controlling their widths and amplitudes (in the case of the bipolar pulse signal, respective widths and amplitudes of its positive and negative sides). Vb is given as a reference potential from a terminal 259, and a bipolar pulse signal is realized as a relative change therefrom. Vb is made to agree with the organism ground level. In the case of the unipolar pulse signal, Vb is made to agree with the substrate potential, and in the case of the bipolar pulse signal, Vb is set at an intermediate level between the supply potential and the substrate potential. Clock pulse signals are inputted to the clk terminal 254, a Φ1 terminal 260, a Φ2 terminal 261, and a stimulus terminal 262. The clock pulse signals Φ1 and Φ2 are operated complementarily.

In addition, in the case where the bipolar pulse signal is outputted, its amplitude on the negative side becomes Vb, while its amplitude on the positive side becomes Vdd'−Vb. In the case of the unipolar pulse signal, its amplitude becomes Vdd'.

In this pulse-number modulation system, since the pulse signal is outputted at a fixed frequency, specific cells can be stimulated stably. In addition, since the quantity of incoming light is expressed by the number of pulses with the amplitude fixed, by adjusting the stimulation intensity it is possible to cope extensively with cells ranging from those exhibiting analog-wise relaxation to those exhibiting digital-wise relaxation. Since the output of the photoelectric conversion portion is a digital value (the inverter output is the output of the photoelectric conversion portion), pulse shaping of a digital or hybrid digital-analog system is facilitated.

In addition, since the bipolar pulse signal is generated by using inverters in the circuit of the sixth embodiment, both injection and pumping of charge can be executed effectively. It should be noted that this circuit can be used in the pulse frequency modulation system as well.

Although in the foregoing embodiments only one pixel circuit has been shown, it goes without saying that similar effects are demonstrated by a system in which a plurality of these pixel circuits are mounted on an identical substrate or separately. In addition, as the substrate, a high polymer or other similar organic material or a metal may be used other than a semiconductor. Still alternatively, it is possible to use a material in which an insulator is interposed, such as silicon on insulator (SOI) or silicon on sapphire (SOS).

Although the invention has been described in detail and with reference to specific embodiments, it is apparent to those skilled in the art that various modifications and corrections may be made without departing from the spirit and scope of the invention.

This application is based on Japanese Patent Application (Japanese Patent Application No. 2001-055772) filed on Feb. 28, 2001 and Japanese Patent Application (Japanese Patent Application No. 2001-268074) filed on Sep. 4, 2001, and their contents are incorporated herein by way of reference.

INDUSTRIAL APPLICABILITY

As described above, in the invention, it is possible to provide an intraocular implant-type vision stimulating unit which is highly sensitive, compact, and low power consumptive. In addition, it is possible to provide an intraocular implant-type vision stimulating unit which is capable of outputting a bipolar pulse signal in a simple constitution.

The invention claimed is:

1. An intraocular implant-type vision stimulating unit for artificially generating the vision or a portion of the vision, comprising:
 a photoelectric conversion circuit which converts incoming light into an electrical signal;
 a pulse conversion circuit which converts the electrical signal outputted from the photoelectric conversion circuit into an electric pulse signal of a frequency corresponding to a magnitude of the electrical signal, and outputs the electric pulse signal;
 a waveform shaping circuit which converts the pulse signal outputted from the pulse conversion circuit into a bipolar pulse signal, and outputs the bipolar pulse signal;
 a power supply circuit which supplies electric power to each of the circuits,
 wherein the bipolar pulse signal is imparted to a retinal region through an electrode.

2. The intraocular implant-type vision stimulating unit according to claim 1, wherein the photoelectric conversion circuit, the pulse conversion circuit, and the waveform shaping circuit are implanted beneath the retina.

3. The intraocular implant-type vision stimulating unit according to claim 1, wherein the pulse conversion circuit includes a voltage control circuit which controls a bias voltage to the photoelectric conversion circuit, a pulse circuit converts the electrical signal outputted from the photoelectric conversion circuit into the electric pulse signal, and a coupling circuit which couples the pulse signal outputted from the pulse circuit to the voltage control circuit.

4. The intraocular implant-type vision stimulating unit according to claim 3, wherein the pulse circuit includes an inverter or a Schmitt trigger whose input voltage is an output voltage of the photoelectric conversion circuit, and the coupling circuit connects a final output side of the pulse circuit and the voltage control circuit.

5. The intraocular implant-type vision stimulating unit according to claim 4, wherein as the inverter or the Schmitt trigger of the pulse circuit, a plurality of inverters or Schmitt triggers are connected in series in an odd number.

6. The intraocular implant-type vision stimulating unit according to claim 4, wherein the voltage control circuit includes a resistor inserted in series between the photoelectric conversion circuit and the coupling circuit, and a capacitor inserted in parallel with the photoelectric conversion circuit.

7. The intraocular implant-type vision stimulating unit according to claim 6, wherein the resistor includes a transistor whose resistance value is variable.

8. The intraocular implant-type vision stimulating unit according to claim 3, wherein the voltage control circuit includes transistors for switching which are respectively connected to a bias power supply of the power supply circuit, the photoelectric conversion circuit, and the coupling circuit.

9. The intraocular implant-type vision stimulating unit according to claim 1, wherein the waveform shaping circuit includes a differentiating circuit which outputs the pulse signal outputted from the pulse conversion circuit as a pulse signal having a differential waveform.

10. The intraocular implant-type vision stimulating unit according to claim 9, wherein the differentiating circuit includes a resistor and a capacitor.

11. The intraocular implant-type vision stimulating unit according to claim 10, wherein the resistor includes a transistor whose resistance value is variable.

12. The intraocular implant-type vision stimulating unit according to claim 1, wherein the power supply circuit includes at least one of a circuit which supplies electric power from a wiring physically connected to an outside, a circuit which supplies electric power by making use of electromagnetic waves from the outside, and a circuit which supplies electric power by generating electricity by the heat of a human body.

13. The intraocular implant-type vision stimulating unit according to claim 1, wherein the pulse conversion circuit includes a frequency modulation circuit which sets the frequency of the pulse signal to a substantially fixed level when the magnitude of the electrical signal outputted from the photoelectric conversion circuit is not more than a first reference value or not less than a second reference value greater than the first reference value, and varies the frequency of the pulse signal in correspondence with the magnitude of the electrical signal when the magnitude of the electrical signal is not less than the first reference value and not more than the second reference value.

14. The intraocular implant-type vision stimulating unit according to claim 13, wherein the pulse conversion circuit further includes an amplitude modulation circuit which varies an amplitude of the pulse signal in correspondence with the magnitude of the electrical signal when the magnitude of the electrical signal outputted from the photoelectric conversion circuit is not more than the first reference value or not less than the second reference value, and sets the amplitude of the pulse signal to a substantially fixed level when the magnitude of the electrical signal is not less than the first reference value and not more than the second reference value.

15. The intraocular implant-type vision stimulating unit according to claim 13, wherein the frequency modulation circuit includes a voltage control circuit which controls a bias voltage to the photoelectric conversion circuit, an odd number of inverters or Schmitt triggers whose input voltage is an output voltage of the photoelectric conversion circuit, and a coupling circuit which couples the pulse signal outputted from the inverter or the Schmitt trigger to the voltage control circuit, and is arranged to set a lower limit frequency by regulating a charging leak source and a discharging leak source with respect to the photoelectric conversion circuit, and to set an upper limit frequency by providing a frequency filter before or after the inverter or the Schmitt trigger.

16. The intraocular implant-type vision stimulating unit according to claim 1, further comprising:

a waveform memory which stores a predetermined electrical stimulation waveform; and a timing control circuit which reads the electrical stimulation waveform from the waveform memory by obtaining an output of the pulse signal from the pulse conversion circuit.

* * * * *